United States Patent
Faller et al.

(10) Patent No.: US 8,603,138 B2
(45) Date of Patent: Dec. 10, 2013

(54) USE OF AN ADHESIVE TO TREAT INTRALUMINAL BLEEDING

(75) Inventors: Craig N. Faller, Milford, OH (US); Wells D. Haberstitch, Loveland, OH (US); Donna L. Korvick, Maineville, OH (US); Bennie Thompson, Cincinnati, OH (US); Douglas J. Turner, Cincinnati, OH (US); Anil K. Nalagatla, Mason, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1572 days.

(21) Appl. No.: 11/538,571

(22) Filed: Oct. 4, 2006

(65) Prior Publication Data

US 2009/0143818 A1 Jun. 4, 2009

(51) Int. Cl.
*A61B 17/08* (2006.01)
*A61D 1/00* (2006.01)

(52) U.S. Cl.
USPC .......................................... 606/216

(58) Field of Classification Search
USPC ............... 606/213–221, 151–158; 604/35
See application file for complete search history.

(56) References Cited

U.S. PATENT DOCUMENTS

| | | |
|---|---|---|
| 3,805,793 A | 4/1974 | Wright |
| 4,735,616 A | 4/1988 | Eibl et al. |
| 4,766,898 A | 8/1988 | Hardy et al. |
| 4,874,368 A | 10/1989 | Miller et al. |
| 5,004,469 A | 4/1991 | Palmieri et al. |
| 5,154,320 A | 10/1992 | Bolduc |
| 5,254,113 A | 10/1993 | Wilk |
| 5,312,333 A | 5/1994 | Churinetz et al. |
| 5,324,305 A | 6/1994 | Kanner |
| 5,372,585 A | 12/1994 | Tiefenbrun et al. |
| 5,443,481 A | 8/1995 | Lee |
| 5,474,540 A | 12/1995 | Miller et al. |
| 5,529,577 A | 6/1996 | Hammerslag |
| 5,582,596 A | 12/1996 | Fukunaga et al. |
| 5,605,541 A | 2/1997 | Holm |
| 5,718,711 A | 2/1998 | Berenstein et al. |
| 5,752,965 A | 5/1998 | Francis et al. |

(Continued)

FOREIGN PATENT DOCUMENTS

| | | |
|---|---|---|
| EP | 0716833 | 6/1996 |
| EP | 1078600 | 2/2001 |

(Continued)

OTHER PUBLICATIONS

English Abstract of Japanese Patent No. JP 10262986, 1998.

(Continued)

*Primary Examiner* — Melanie Tyson (57) ABSTRACT

A surgical device to stanch the flow of blood is disclosed. The surgical device can place an implantable adhesive over or around varices or other bleeders. The surgical device has a vacuum system for capturing tissue and an adhesive system to apply adhesive to the captured tissue. A vacuum chamber is used to contact tissue and contains a chamber therein for the reception of tissue. An adhesive applicator is provided within the vacuum chamber and moves longitudinally therein to apply adhesive to tissue. The surgical device can apply an adhesive patch to tissue or inject adhesive into tissue. Alternately, an adhesive actuator and a chemical agent can be dispensed to tissue within the vacuum chamber.

19 Claims, 10 Drawing Sheets

(56) References Cited

U.S. PATENT DOCUMENTS

| | | |
|---|---|---|
| 5,759,169 A | 6/1998 | Marx |
| 5,759,171 A | 6/1998 | Coelho et al. |
| 5,814,022 A | 9/1998 | Antanavich et al. |
| 5,844,087 A | 12/1998 | Zimmerman et al. |
| 5,895,412 A | 4/1999 | Tucker |
| 5,928,611 A | 7/1999 | Leung |
| 5,980,548 A * | 11/1999 | Evans et al. ............... 606/185 |
| 5,981,621 A | 11/1999 | Clark et al. |
| 6,007,515 A | 12/1999 | Epstein et al. |
| 6,010,714 A | 1/2000 | Leung et al. |
| 6,055,828 A | 5/2000 | Rivera et al. |
| 6,099,807 A | 8/2000 | Leung |
| 6,113,571 A | 9/2000 | Zinger et al. |
| 6,143,352 A | 11/2000 | Clark et al. |
| 6,143,805 A | 11/2000 | Hickey et al. |
| 6,162,239 A | 12/2000 | Manhes |
| 6,174,919 B1 | 1/2001 | Hickey |
| 6,183,593 B1 | 2/2001 | Narang et al. |
| 6,206,905 B1 | 3/2001 | Holm et al. |
| 6,217,603 B1 | 4/2001 | Clark et al. |
| 6,228,051 B1 | 5/2001 | Trumbull |
| 6,234,994 B1 | 5/2001 | Zinger |
| 6,245,933 B1 | 6/2001 | Malofsky et al. |
| 6,280,399 B1 | 8/2001 | Rossin et al. |
| 6,283,933 B1 | 9/2001 | D'Alessio et al. |
| 6,302,898 B1 | 10/2001 | Edwards et al. |
| 6,306,243 B1 | 10/2001 | Clark et al. |
| 6,310,166 B1 | 10/2001 | Hickey et al. |
| 6,322,852 B1 | 11/2001 | Leung |
| 6,325,810 B1 | 12/2001 | Hamilton et al. |
| 6,340,097 B1 | 1/2002 | D'Alessio et al. |
| 6,352,704 B1 | 3/2002 | Nicholson et al. |
| 6,372,313 B1 | 4/2002 | D'Alessio et al. |
| 6,376,019 B1 | 4/2002 | Leung |
| 6,394,975 B1 | 5/2002 | Epstein |
| 6,394,982 B1 | 5/2002 | Ehrenfels |
| 6,398,797 B2 | 6/2002 | Bombard et al. |
| 6,412,639 B1 | 7/2002 | Hickey |
| 6,420,590 B1 | 7/2002 | Badejo et al. |
| 6,425,704 B2 | 7/2002 | Voiers et al. |
| 6,428,233 B1 | 8/2002 | Clark et al. |
| 6,428,234 B1 | 8/2002 | Bobo et al. |
| 6,432,084 B1 | 8/2002 | Levinson et al. |
| 6,433,096 B1 | 8/2002 | Hickey et al. |
| 6,439,789 B1 | 8/2002 | Ballance et al. |
| 6,454,739 B1 | 9/2002 | Chang |
| 6,455,064 B1 | 9/2002 | Narang et al. |
| 6,458,095 B1 | 10/2002 | Wirt et al. |
| 6,461,361 B1 | 10/2002 | Epstein |
| 6,461,367 B1 | 10/2002 | Kirsch et al. |
| 6,464,663 B1 | 10/2002 | Zinger |
| 6,468,520 B1 | 10/2002 | Rowe et al. |
| 6,471,670 B1 | 10/2002 | Enrenfels et al. |
| 6,478,191 B1 | 11/2002 | D'Alessio et al. |
| 6,488,197 B1 | 12/2002 | Whitman |
| 6,488,650 B1 | 12/2002 | Epstein et al. |
| 6,488,944 B2 | 12/2002 | Narang |
| 6,491,201 B1 | 12/2002 | Whitman |
| 6,494,896 B1 * | 12/2002 | D'Alessio et al. ............ 606/213 |
| 6,512,023 B1 | 1/2003 | Malofsky et al. |
| 6,527,749 B1 | 3/2003 | Roby et al. |
| 6,540,716 B1 | 4/2003 | Holm |
| 6,540,789 B1 | 4/2003 | Silverman et al. |
| 6,547,467 B2 | 4/2003 | Quintero |
| 6,565,840 B1 | 5/2003 | Clark et al. |
| 6,579,469 B1 | 6/2003 | Nicholson et al. |
| 6,585,967 B2 | 7/2003 | Narang et al. |
| 6,589,269 B2 * | 7/2003 | Zhu et al. ................. 606/214 |
| 6,592,281 B2 | 7/2003 | Clark et al. |
| 6,595,940 B1 | 7/2003 | D'Alessio et al. |
| 6,602,496 B2 | 8/2003 | Hedgpeth et al. |
| 6,605,667 B1 | 8/2003 | Badejo et al. |
| 6,607,631 B1 | 8/2003 | Badejo et al. |
| 6,613,020 B1 | 9/2003 | Holm et al. |
| 6,616,019 B2 | 9/2003 | D'Alessio et al. |
| 6,620,846 B1 | 9/2003 | Jonn et al. |
| 6,637,967 B2 | 10/2003 | Bobo et al. |
| 6,666,873 B1 | 12/2003 | Cassell |
| 6,676,322 B1 | 1/2004 | Leung |
| 6,681,797 B2 | 1/2004 | Mannhart |
| 6,695,199 B2 | 2/2004 | Whitman |
| 6,705,790 B2 | 3/2004 | Quintero et al. |
| 6,743,858 B2 | 6/2004 | Hickey et al. |
| 6,746,667 B2 | 6/2004 | Badejo et al. |
| 6,748,950 B2 | 6/2004 | Clark et al. |
| 6,764,467 B1 * | 7/2004 | Roby et al. ............... 604/191 |
| 6,767,552 B2 | 7/2004 | Narang |
| 6,779,657 B2 | 8/2004 | Mainwaring et al. |
| 6,783,514 B2 | 8/2004 | Tovey et al. |
| 6,802,416 B1 | 10/2004 | D'Alessio et al. |
| 6,802,822 B1 | 10/2004 | Dodge |
| 6,811,341 B2 | 11/2004 | Crane |
| D500,085 S | 12/2004 | Cotter et al. |
| 6,837,027 B2 | 1/2005 | Hickey |
| 6,863,660 B2 | 3/2005 | Marx |
| 6,884,232 B1 | 4/2005 | Hagmann et al. |
| 6,896,684 B2 | 5/2005 | Monassevitch et al. |
| 6,896,838 B2 | 5/2005 | D'Alessio |
| 6,921,381 B2 | 7/2005 | Spero et al. |
| 6,942,875 B2 | 9/2005 | Hedgpeth |
| 6,960,040 B2 | 11/2005 | D'Alessio et al. |
| 6,997,941 B2 | 2/2006 | Sharkey et al. |
| 7,008,442 B2 | 3/2006 | Brightbill |
| 7,037,344 B2 | 5/2006 | Kagan et al. |
| 7,044,979 B2 | 5/2006 | Silverman et al. |
| 7,056,277 B2 | 6/2006 | Silverman et al. |
| 7,128,241 B2 | 10/2006 | Leung |
| 7,138,135 B2 | 11/2006 | Chen et al. |
| 7,217,254 B2 | 5/2007 | Kirwan et al. |
| 7,238,195 B2 | 7/2007 | Viola |
| 7,293,562 B2 * | 11/2007 | Malecki et al. ............. 128/898 |
| 7,306,390 B2 | 12/2007 | Quintero et al. |
| 7,331,463 B2 | 2/2008 | Hickey |
| 7,338,434 B1 * | 3/2008 | Haarstad et al. ............. 600/37 |
| 7,431,730 B2 | 10/2008 | Viola |
| 7,517,356 B2 | 4/2009 | Heinrich |
| 7,608,086 B2 | 10/2009 | Tanaka et al. |
| 7,635,372 B2 | 12/2009 | Hamilton |
| 7,708,684 B2 | 5/2010 | Demarais |
| 7,892,220 B2 | 2/2011 | Faller et al. |
| 7,896,893 B2 | 3/2011 | Laufer et al. |
| 7,909,808 B2 | 3/2011 | Stenton |
| 7,914,511 B2 | 3/2011 | Ortiz et al. |
| 8,287,202 B2 | 10/2012 | Goodman et al. |
| 2002/0037310 A1 | 3/2002 | Jonn et al. |
| 2002/0048480 A1 | 4/2002 | D'Alessio et al. |
| 2002/0055573 A1 | 5/2002 | Malofsky et al. |
| 2002/0065336 A1 | 5/2002 | Hickey et al. |
| 2002/0091299 A1 * | 7/2002 | Silverman et al. ............ 600/29 |
| 2002/0119184 A1 | 8/2002 | Nicholson et al. |
| 2002/0147462 A1 | 10/2002 | Mair et al. |
| 2002/0165483 A1 | 11/2002 | Miller et al. |
| 2002/0173770 A1 | 11/2002 | Flory et al. |
| 2003/0031499 A1 | 2/2003 | Heard et al. |
| 2003/0032833 A1 | 2/2003 | Badejo et al. |
| 2003/0032967 A1 | 2/2003 | Park et al. |
| 2003/0039781 A1 | 2/2003 | D'Alessio et al. |
| 2003/0060380 A1 | 3/2003 | Ayarza et al. |
| 2003/0080151 A1 | 5/2003 | D'Alessio et al. |
| 2003/0082116 A1 | 5/2003 | Badejo et al. |
| 2003/0149128 A1 | 8/2003 | Malofsky et al. |
| 2003/0202956 A1 | 10/2003 | Clark et al. |
| 2004/0111115 A1 | 6/2004 | Maw |
| 2004/0137067 A1 | 7/2004 | Narang et al. |
| 2004/0151688 A1 | 8/2004 | Sherbondy et al. |
| 2004/0190975 A1 | 9/2004 | Goodman et al. |
| 2004/0223932 A1 | 11/2004 | Hedgpeth et al. |
| 2004/0223946 A1 | 11/2004 | Kidd et al. |
| 2005/0021085 A1 | 1/2005 | Abrams et al. |
| 2005/0042266 A1 | 2/2005 | Narang |
| 2005/0047846 A1 | 3/2005 | Narang et al. |
| 2005/0070935 A1 | 3/2005 | Ortiz |
| 2005/0070939 A1 | 3/2005 | Beaupre |
| 2005/0147457 A1 | 7/2005 | Badejo et al. |

(56) References Cited

U.S. PATENT DOCUMENTS

| | | |
|---|---|---|
| 2005/0171556 A1 | 8/2005 | Murphy |
| 2005/0182443 A1 | 8/2005 | Jonn et al. |
| 2005/0256446 A1 | 11/2005 | Criscuolo et al. |
| 2006/0009099 A1 | 1/2006 | Jonn et al. |
| 2008/0195225 A1 | 8/2008 | Silverman et al. |
| 2008/0234834 A1 | 9/2008 | Meade et al. |

FOREIGN PATENT DOCUMENTS

| | | |
|---|---|---|
| JP | 62-195864 | 2/1989 |
| JP | A 64-049567 | 2/1989 |
| JP | A 64-059553 | 2/1989 |
| JP | A 05-064642 | 3/1993 |
| JP | 10262986 | 10/1998 |
| JP | 2000217830 | 8/2000 |
| JP | 2001157716 | 6/2001 |
| JP | 2001190558 | 7/2001 |
| JP | 2002233581 | 8/2002 |
| JP | T 2002535065 | 10/2002 |
| JP | 2003126268 | 5/2003 |
| JP | 2005028009 | 2/2005 |
| JP | 2005169125 | 6/2005 |
| WO | WO 92/09651 | 6/1992 |
| WO | WO 95/31137 | 11/1995 |
| WO | WO 98/41154 | 9/1998 |
| WO | WO 99/17833 | 4/1999 |
| WO | WO 99/30629 | 6/1999 |
| WO | WO 99/55394 | 11/1999 |
| WO | WO 00/09074 | 2/2000 |
| WO | WO 00/53339 | 9/2000 |
| WO | WO 03/088845 | 9/2000 |
| WO | WO 01/12257 | 2/2001 |
| WO | WO 01/24869 | 4/2001 |
| WO | WO 01/62158 | 8/2001 |
| WO | WO 01/62162 | 8/2001 |
| WO | WO 01/62333 | 8/2001 |
| WO | WO 02/067785 | 9/2002 |
| WO | WO 02/085218 | 10/2002 |
| WO | WO 03/011145 | 2/2003 |
| WO | 2006108050 A2 | 10/2006 |
| WO | 2007002227 A2 | 1/2007 |

OTHER PUBLICATIONS

English Abstract of Japanese Patent No. JP 2000217830, 2002.
English Abstract of Japanese Patent No. JP 2011157716, 2011.
English Abstract of Japanese Patent No. JP 2001190558, 2011.
English Abstract of Japanese Patent No. JP 2002233581, 2002.
English Abstract of Japanese Patent No. JP 2003126268, 2003.
English Abstract of Japanese Patent No. JP 2005028009, 2005.
English Abstract and Machine Translation of Japanese Patent No. JP 2005169125, 2005.
English Abstract of Japanese Patent Application No. JP A 05-064642.
English Abstract of Japanese Patent Publication No. JP A 64-049567.
English Abstract of Japanese Patent Publication No. JP A 64-059553.
English Abstract and Machine Translation of Japanese Patent No. JP T 2002535065.
English Translation of Japanese Office Action dated Dec. 4, 2012 for Application No. JP 2007-260159.
European Search Report, dated Feb. 1, 2008, Applicaton No. EP07253946.

* cited by examiner

USE OF AN ADHESIVE TO TREAT INTRALUMINAL BLEEDING

FIELD OF THE INVENTION

The present invention relates, in general, to devices for the treatment and control of bleeding, and in particular, to devices using adhesives for the treatment of bleeding.

BACKGROUND OF THE INVENTION

There are several clinical situations or disease states that would result in the small hemorrhages from varices, veins and small arteries. One possible use of this invention is the treatment of esophageal variceal bleeding which has not responded to typical endoscopic therapy, pharmacological therapy, or a surgical shunt.

Variceal bleeding in the esophagus is caused by portal hypertension. Portal hypertension is an increase in the pressure within the portal vein (the vein that carries blood from the digestive organs to the liver). This increase in pressure is caused by a blockage in the blood flow throughout the liver. Increased pressure in the portal vein causes enlarged veins (varices) to develop across the esophagus and stomach to bypass the blockage. The walls of the varices become fragile and can rupture and bleed easily. In some cases this bleeding can result in massive uncontrollable bleeding, which left unchecked, could cause severe health issues. Alternately, surgical trauma or other trauma to the esophageal region could also result in a similar bleeding situation.

If the patient has gastric reflux disease, the situation can be exacerbated by acid reflux intrusion into the esophagus. This intrusion of stomach acids can cause thinning or removal of the mucosal lining of the esophagus and could expose the underlying vein or varices structures to the chronic acid reflux. Enlarged veins have thinner walls, and acid reflux exposure can thin them further. In some cases, coughing or vomiting might overload the thinned vein or varices, cause a bleeding cycle to occur, and require surgical treatment.

Enlarged vein structures or varices are not limited to the esophageal areas and neither are the veinus and arterial stresses induced by coughing, vomiting, trauma, pregnancy, obesity, prolonged standing, hard stools, or other bodily functions. As a consequence, varices are found in hemorrhoids, varicoceles, and varicose veins in areas such as the legs, stomach, and feet. Hemorrhages can be found at these sites, but can occur in any arena where small veins and arteries are near the surface of a structure that is being subjected to stresses or trauma.

Consequently, a significant need exists for a surgical device that can atraumatically acquire the bleeding site, prevent further damage to the vein or artery, and place a barrier at the bleeding site to stop the bleeding, and leave a barrier that is secure to prevent reoccurrence of the bleeding cycle.

BRIEF SUMMARY OF THE INVENTION

In accordance with the present invention, there is provided a surgical device for staunching the flow of blood from tissue. The surgical device comprises an adhesive implantable in the body and a vacuum system for capturing tissue. An adhesive system is provided to apply the adhesive to tissue captured within the vacuum system to staunch the flow of blood.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Enlarged vein structures or varices are found within the body in a variety of locations. These enlarged vein structures can include arteries, and have thinner wall structures that can cause bleeders when subjected to trauma, or disease conditions such as portal hypertension or hemorrhoids. With portal hypertension, the enlarged varices about the esophagus can rupture and cause chronic bleeding into the esophagus. If severe, the condition can require surgical intervention to staunch the bleeding and leave a structure in place that can prevent further damage to the vein or artery.

Figure 1:
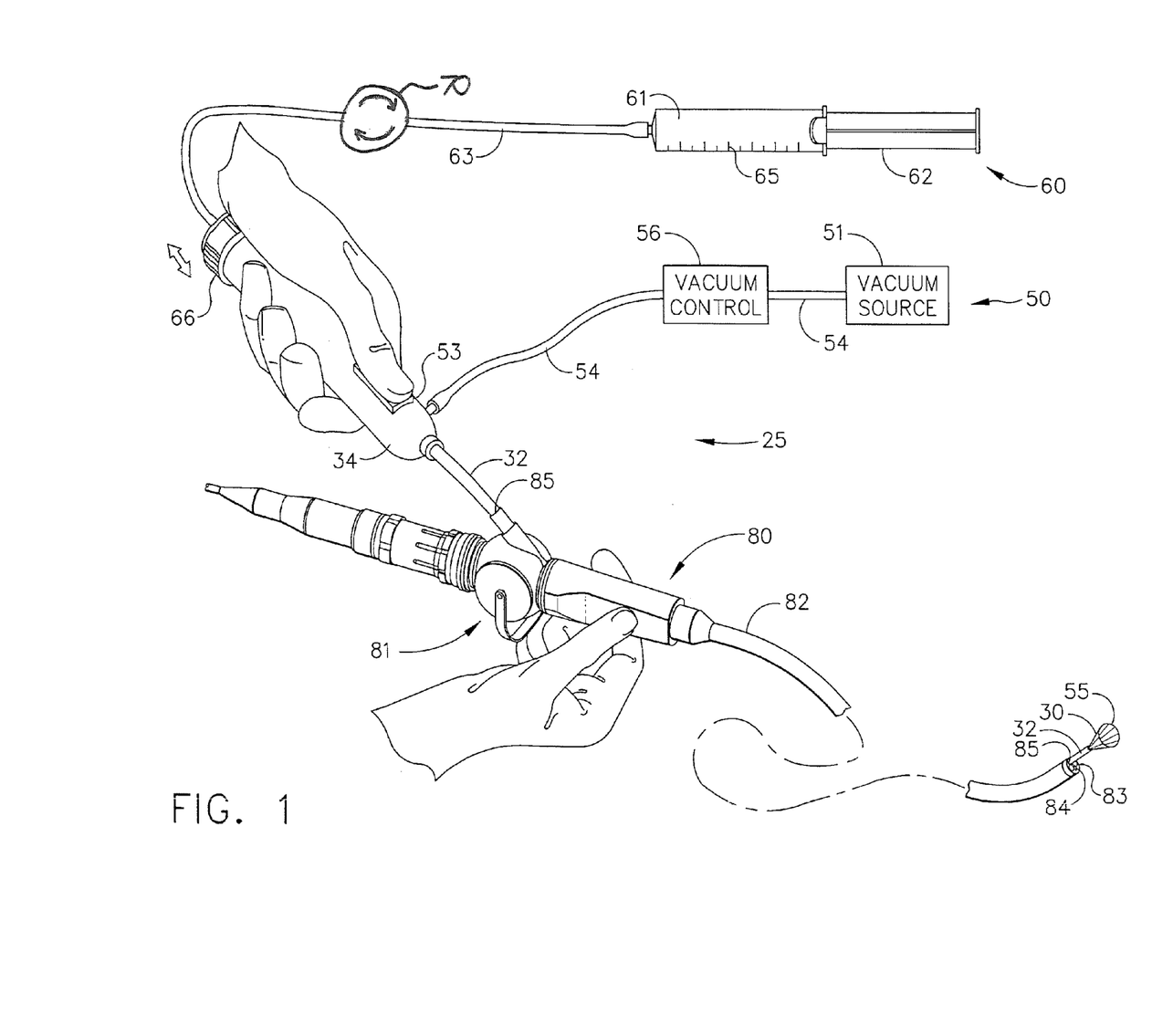
FIG. 1 is an isometric view of a surgical device inserted into an endoscope with a vacuum source and a vacuum control and an adhesive system attached.
Figure 2:
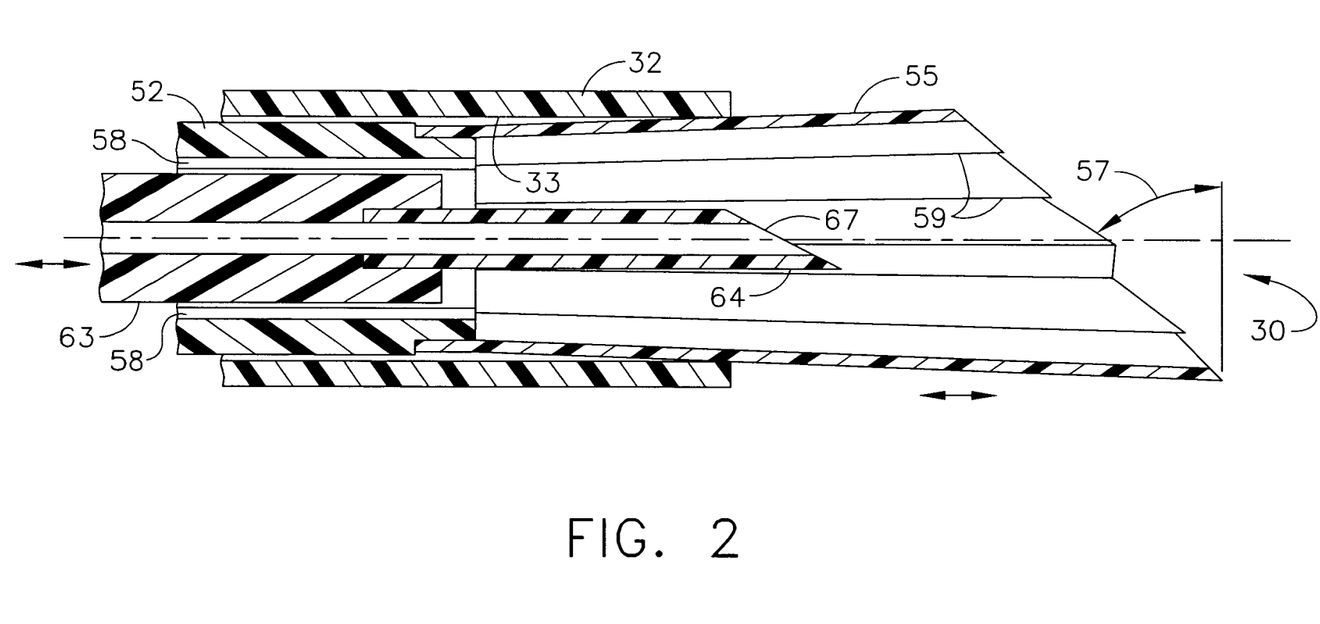
FIG. 2 is a cross sectional view of an end effector of the surgical device of FIG. 1.

FIGS. 1 and 2 illustrates an example of a surgical device 25 capable of stopping the flow of blood with an adhesive 65 at a surgical site such as the esophagus. Surgical device 25 can control blood loss by capturing tissue with a tissue acquisition system or vacuum system, and then using an adhesive injection system to inject an adhesive into or onto the captured tissue to staunch blood loss, place a barrier about the varices, and protect the wound site. The surgical device 25 as shown in FIG. 1 has a distal portion that is small in cross section so it can be inserted into a working channel 85 of an endoscope 80. Endoscope 80 is a common surgical access instrument that has a scope handle 81, a steerable flexible shaft 82, a viewing element 84 at a distal tip 83 to view the surgical site, and the working channel 85 extending from handle 81 to distal tip 83. Endoscopes are commonly inserted into the mouth or anus to use natural body orifices to gain access to surgical sites within the patient. Surgical device 25 generally extends from a handle 34 to an end effector 30. FIG. 1 shows the handle 34 extending from a proximal end of the working channel 85 and the end effector 30 extending from a distal end of the working channel 85. The surgical device 25 is positionable with respect to the operative channel 85 of endoscope 80 in rotation, insertion, and extraction. A flexible shaft 32 operatively couples end effector 30 to the handle 34.

Vacuum System

The vacuum system 50 of the surgical device 25 has a vacuum source 51 and a vacuum control 56 to control the delivery of vacuum to the handle 34. Vacuum is supplied through a hose 54 extending from vacuum control 56. A longitudinally moveable vacuum cannula 52 (FIG. 2) is operably connected to hose 54 and extends from handle 34, through flexible shaft 32, to the end effector 30. Vacuum cannula 52 moves proximally and distally within handle 34 and flexible shaft 32 in response to proximal and distal manipulation of chamber control 53 on handle 34. A conical vacuum chamber 55 attaches to a distal tip of the vacuum cannula 52 and is operably coupled to vacuum source 51 and vacuum control 56 by vacuum cannula 52 and hose 54. As shown in FIG. 2, vacuum passageways 58 are provided in vacuum cannula 52 to conduct vacuum to vacuum chamber 55.

Figure 3:
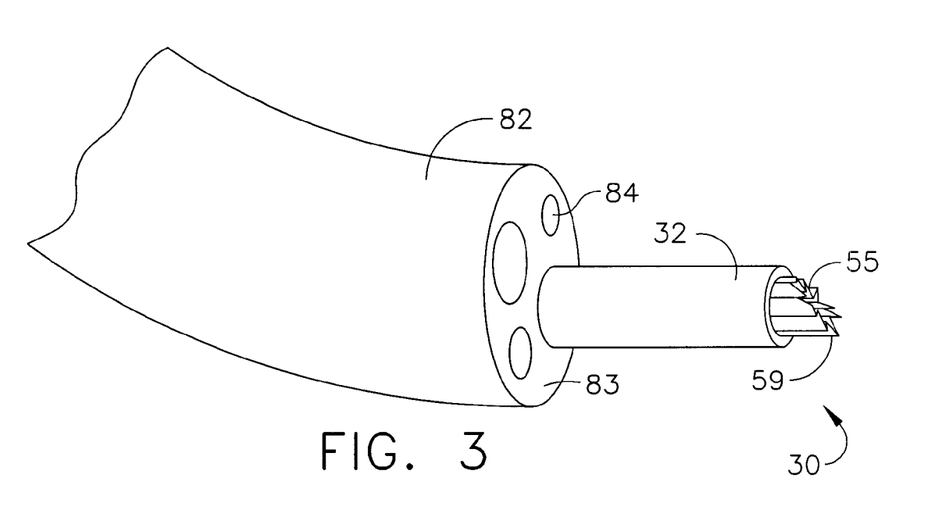
FIG. 3 is an enlarged isometric view of a distal end of the endoscope with the end effector of the surgical device extending therefrom and an unexpanded vacuum chamber partially extending from the end effector.
Figure 4:
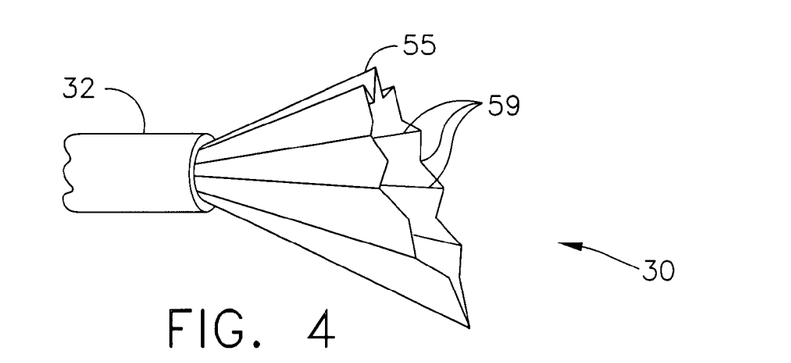
FIG. 4 is an enlarged isometric view of the end effector of the surgical device of FIG. 3 with the vacuum chamber in a partially opened configuration.

Vacuum chamber 55 is best shown in FIGS. 1-5, and is a collapsible and expandable structure. Vacuum chamber 55 has a fully open conical shape of FIGS. 1 and 5 and can be collapsed to a partially closed position of FIG. 4, to the nearly closed position of FIG. 3, and to a fully closed cylindrical shape with pleats and folds within flexible shaft 32 (not shown). As vacuum chamber 55 is collapsed, a series of pre-induced folds 59 located about the periphery are used to control collapsing, and are best shown in FIGS. 3 and 4. As shown, vacuum chamber 55 is formed from a spring material that has a naturally open conical shape. In the full open position, the folds 59 could induce local distortion and prevent vacuum chamber 55 from attaining a smooth conical shape.

Figure 5:
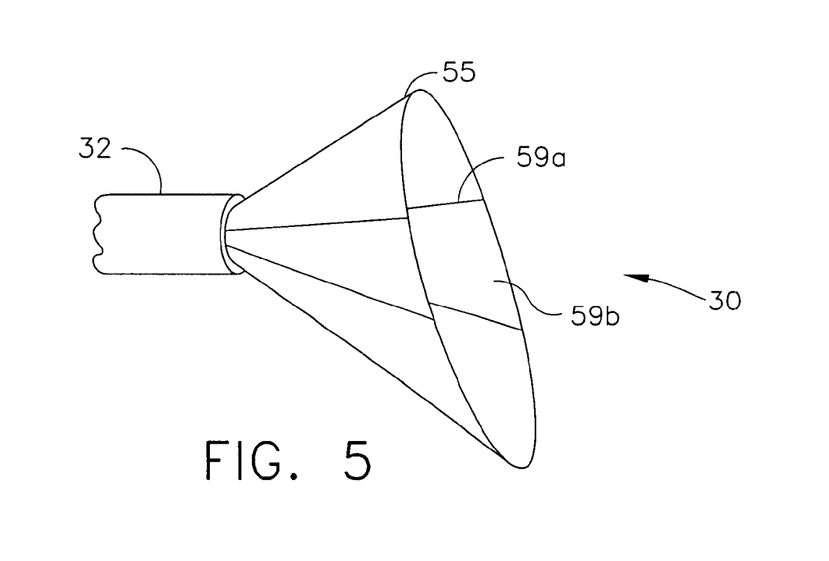
FIG. 5 is an enlarged isometric view of the end effector of the surgical device of FIG. 3 with the vacuum chamber in a fully opened configuration.

Distal and proximal movement of chamber control 53 on handle 34 moves vacuum cannula 52 and attached vacuum chamber 55 distally and proximally relative to flexible shaft 32. Distal movement of vacuum cannula 52 moves vacuum chamber 55 out of the confines of flexible shaft 32 and allows the vacuum chamber 55 to expand. Alternately, proximal motion of a fully open vacuum chamber 55 into flexible shaft 32 closes vacuum chamber 55 by bringing vacuum chamber 55 into camming action with an inner surface 33 of flexible shaft 32. An angle 57 is cut onto a distal end of vacuum chamber 55 to enhance angular contact of the vacuum chamber 55 with the wall of the esophagus, and to ensure a good vacuum seal. To ensure safety and efficacy during insertion into the body and during positioning, vacuum chamber 55 can be withdrawn fully into flexible shaft 32. Vacuum chamber 55 can be constructed from a number of engineering materials such as but not limited to thin sections of engineering thermoplastics such as mylar, silicone, polytetraflouroethylene (Teflon) and the like, or thin sections of metals such as titanium, nitinol or aluminum. Nitinol vacuum chambers 55 could undergo a phase change as they are opened or collapsed. Alternately, by way of example, vacuum chamber 55 can be constructed with an umbrella-like construction as shown in FIG. 5 with a series of ribs 59a joined to a thinner conical section of flexible fabric or film material 59b. Film material 59b could also be springy. Alternately, by way of example, ribs 59a can be constructed as thicker ribs 59a molded onto the film material 59b, rigid separate ribs attached to an opening structure like that used in an umbrella (see FIG. 5), or a springy an umbrella type construction with flexible cantilever spring ribs. The flexible cantilever spring ribs can be pre-bent to expand into a conical rib structure to open the film material 59b. Film material 59b can be materials such as but not limited to rubber compounds such as nitryl, polyethelene, polypropelene, polytetraflouroethylene, papers, and surgical fabrics with or without coatings, or films (not shown) and the like. Additionally, by way of example, a spring could be provided to open the umbrella shape.

Adhesive System

The adhesive system 60 has an adhesive reservoir 61 containing an adhesive 65 and a pump 62. Pump 62 moves adhesive 65 from the adhesive reservoir 61, into an adhesive cannula 63 extending therefrom, and out of an applicator tip 64 at a distal end of adhesive cannula 63. Adhesive cannula 63 of surgical instrument 25 extends from adhesive reservoir 61, passes through handle 34, through flexible shaft 32 into end effector 30, and operably attaches to applicator tip 64. Adhesive cannula 63 is movable proximally and distally by proximal and distal movement of an applicator control 66 located at a proximal end of handle 34. Distal motion of applicator control 66 moves applicator tip 64 distally out of a distal end of flexible shaft 32. Proximal motion of applicator control 66 moves applicator tip 64 and adhesive cannula 63 proximally back into the distal end of the flexible shaft 32. The extension of vacuum chamber 55 and applicator tip 64 from flexible shaft 32 creates the end effector 30.

Additionally, the adhesive system 60 could be a multiple chamber adhesive system 60a containing any number of chambers greater than one. Each chamber can contain contents such as adhesive 65 which can be single or multi-part, an adhesive initiator 68, or alternate chemical agents 69 listed below. For example, a multiple chamber adhesive system 60a could have the adhesive reservoir 61 containing an adhesive 65 and a second chemical agent chamber 61a. Both chambers 61, 61a are operably attached to pump 62 and an alternate adhesive cannula 63a to dispense the contents of chambers 61 and 61a. Alternate adhesive cannula 63a can comprise a dual or multi-lumen tube that distributes both adhesive 65 and adhesive initiators 68 and/or chemical agents 69 from applicators 64, 122 in any combination. A mixer 70 could be placed downstream from pump 62 and pump 62 could contain one or more members operably connected to different chambers. For example, a dual chamber syringe could have dual pistons or pumps to dispense the contents from a chamber. Alternately by way of example, any type of pump could be used such as but not limited to piston, diaphragm, rotary, and siphon. If desired, the contents of both chambers could be applied neat or mixed from applicators 64, 122 (see below).

The cross section of FIG. 2 shows end effector 30 with adhesive cannula 63 slidably moveable in vacuum cannula 52 and surrounded by passageways 58 for the passage of vacuum to vacuum chamber 55. Adhesive tip 64 has a sharp 67 on the distal end and is fixedly attached to longitudinally moveable adhesive cannula 63 and moves in response to movement of the applicator control 66. To prevent unwanted tissue damage from the sharp 67 during insertion into the patient and positioning in the body, adhesive tip 64 is moved proximally into flexible shaft 32 to present the blunt end of flexible shaft 32. Distal motion of applicator control 66 moves adhesive tip 64 and sharp 67 distally to pierce tissue. Activation of pump 22 forces adhesive 65 from the sharp 67 of the adhesive tip 64.

The Adhesive and Compounds

By way of example, adhesive 65 could be a single part or a dual part adhesive that is a polymerizable and/or cross-linkable material such as but not limited to a cyanoacrylate adhesive. The adhesive 65 can be fluid and for example, may be but not limited to a monomeric (including prepolymeric) adhesive composition, a polymeric adhesive composition, or any other natural or artificial biocompatible compound that can adhere to tissue. In embodiments, the monomer may be a 1,1-disubstituted ethylene monomer, e.g., an .alpha.-cyanoacrylate. When cross linked, the cyanoacrylate changes from a liquid to a solid. Cross linked adhesive 76a can be a rigid or flexible and can be non-permeable or permeable. If desired, adhesive 76 can be a single part or dual part adhesive, and/or can contain one or more additives 77. Adhesive 65 can be polymerized by moisture, blood, saline or adhesive initiators 68. Adhesive initiators 68 can also be used to set up or polymerize the adhesive 65 and can be but are not limited to base compounds and the like.

Examples of suitable chemical agents 69 include, such as but are not limited to, image enhancement media, anesthetics, sclerotic or necrosing agents plasticizing agents, thixotropic agents, buffers, catalysts, fillers, micro particles, adhesion initiators, thickeners, solvents, drugs, medicaments, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes, mixtures thereof, and the like. Other suitable single part and dual part adhesives 65, adhesion initiators 68, and chemical agents 69 may be found in United States Application 20040190975 by Goodman et al. which is hereby incorporated by reference in its entirety.

Method of Use

Figure 6:
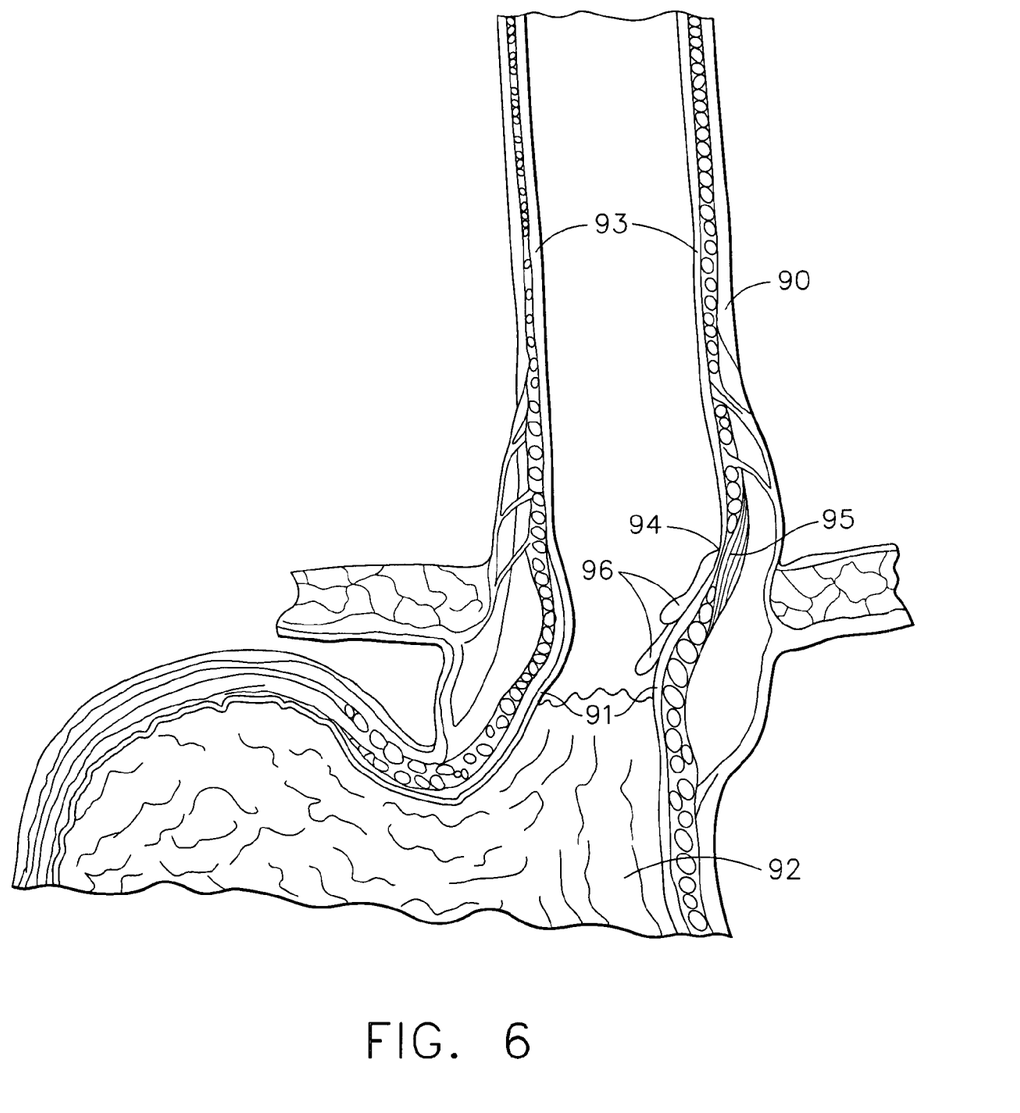
FIG. 6 is a cross sectional view of the esophagus and stomach of a patient and showing a varices with small bleeders close to the inner surface of the esophagus and above the gastroesophageal junction.

FIG. 6 shows an esophagus 90, the gastro-esophageal junction 91 and the stomach 92. A plurality of vascular structures are located about the esophagus 90. The patient has experienced chronic acid reflux which has eroded and thinned the esophagus 90 and a mucosal layer 93 to create a thin area 94 above the gastro-esophageal junction 91 on the right side of the esophagus 90. The patient suffers from portal hypertension which is an increase in the pressure within the portal vein caused by a blockage in the blood flow throughout the liver. This reduced blood flow results in increased pressure in the portal vein and has caused enlarged veins or varices 95 to develop across the esophagus 90 and stomach 92, with one behind thin area 94. The varices 95 are distended and fragile, and can rupture and bleed easily when the patient suffers from severe coughing or vomiting. As shown the varices 95 above the gastroesophageal junction 91 have a bleeder 96. The thin mucosal layer allows acid reflux to reach and irritate the varices 95 which slows or prevents proper healing, as well as providing reduced reinforcement of varices 95.

Figure 7:
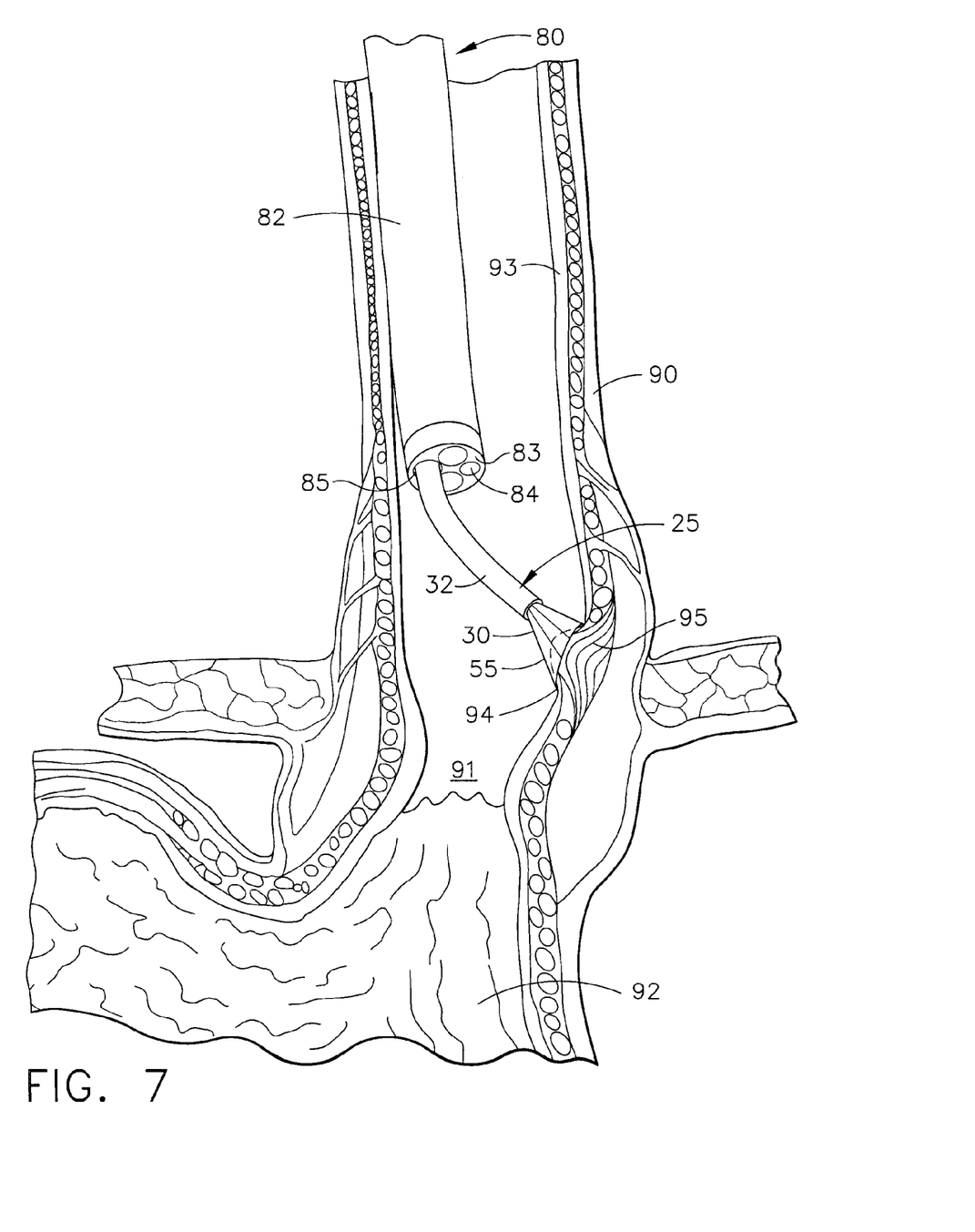
FIG. 7 is the cross sectional view of FIG. 6 with the endoscope and surgical device inserted therein, wherein a fully opened vacuum chamber of the surgical device is placed over the varices.

FIG. 7 shows the flexible shaft 82 of the endoscope 80 inserted into the patients esophagus 90. The end effector 30 of the surgical device 25 extends from the working channel 85 in distal tip 83 of endoscope 80. Viewing element 84 is used to locate the thin area 94 and the bleeders 96 (FIG. 6) in the esophagus 90. The end effector 30 of the surgical device has been extended from the working channel 85 of the endoscope 80 and vacuum chamber 55 has been expanded and placed over thin area 94. A vacuum is being applied from vacuum source 51 to capture the thin area 94 and varices 95 within vacuum chamber 55.

Figure 8:
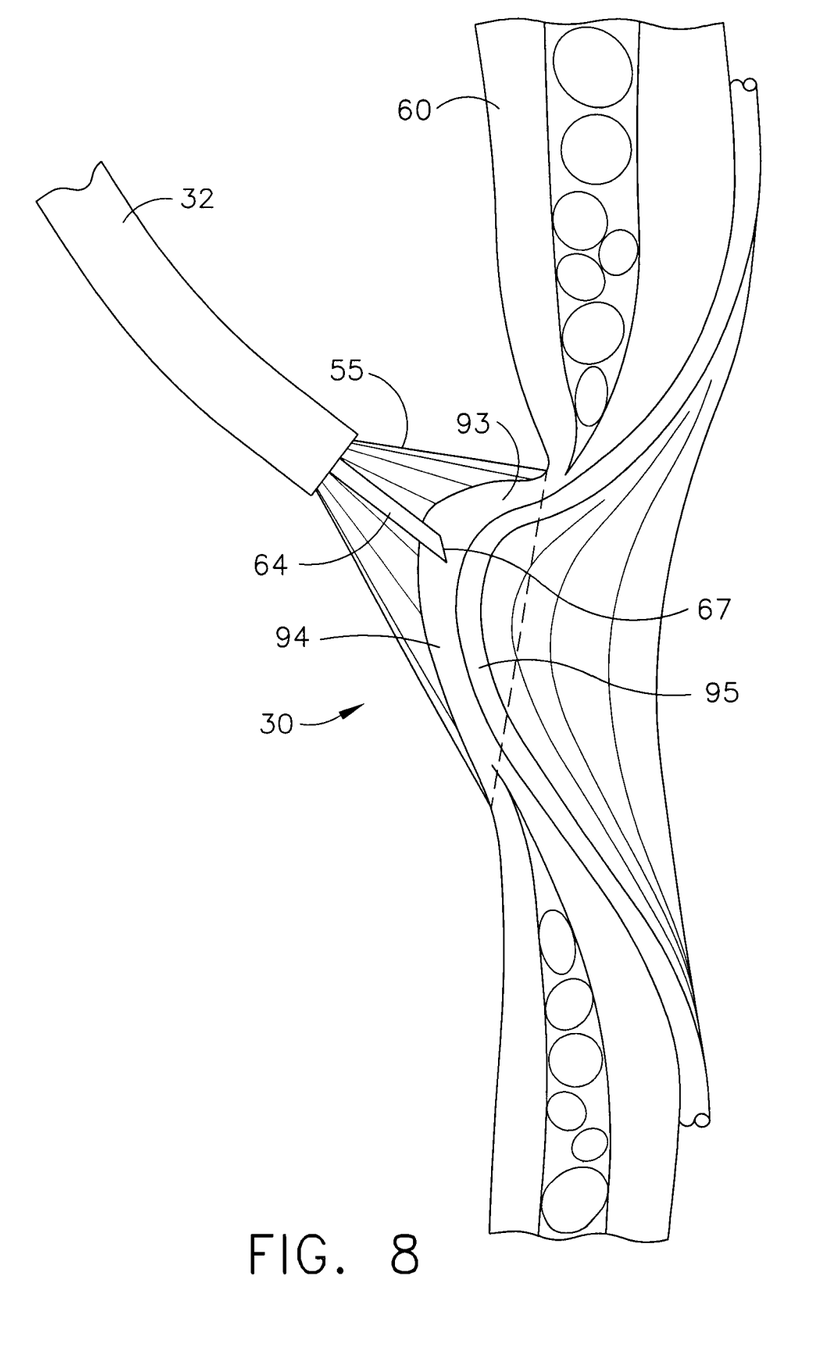
FIG. 8 is a side view of the vacuum chamber of the device drawing a vacuum to pull the varices with the bleeders into the vacuum chamber with an applicator tip of an adhesive system piercing the esophageal wall.

FIG. 8 is a cross section of the end effector 30 on the thin area 94 of the esophageal tissue. Vacuum chamber 55 is capturing and drawing the thin area 94 comprising mucosa 93 and varices 95 into vacuum chamber 55 with the application of vacuum from vacuum source 51. The sharp 67 on applicator tip 64 has been moved distally from flexible shaft 32 and is piercing the mucosal layer 93 and tissue about varices 95.

Figure 9:
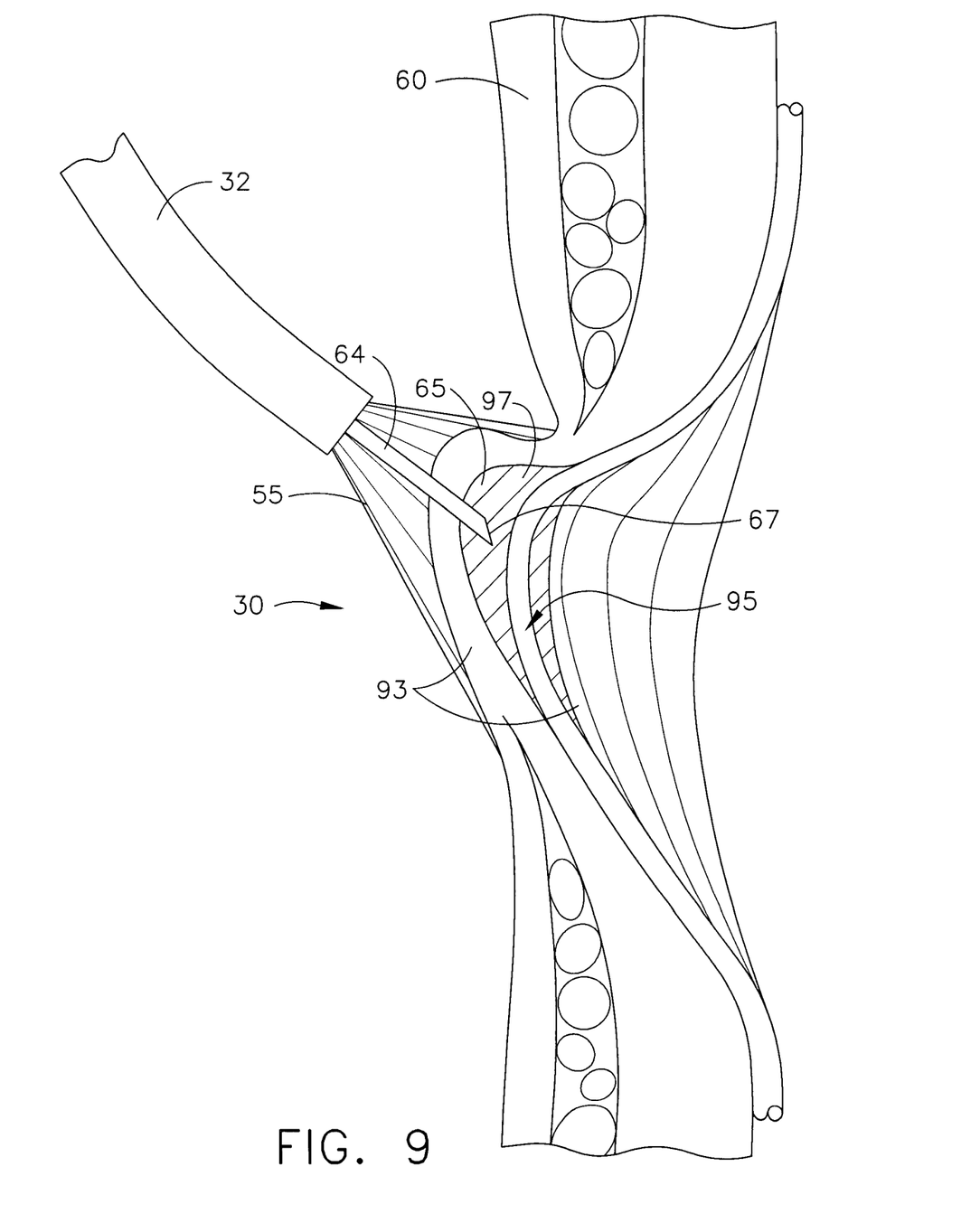
FIG. 9 is the side view of FIG. 8 showing an adhesive being injected about the varices.

FIG. 9 is the cross sectional view of FIG. 8 after the applicator tip 64 is extended further into the esophageal tissue and adhesive 65 has been injected about the varices 95. Adhesive 65 emerges from sharp 67 of applicator tip 64 under pressure from pump 62 and has separated mucosal layers 93 about varices 95. Adhesive 95 begins to set from bodily moisture to stop or staunch the bleeding and creates a protective cap 97 of adhesive about the varices 95. The protective cap 97 is integrated into tissue to prevent falling off, and prevents the patient from experiencing additional chronic bleeding. To remove the surgical device 25, the applicator tip 64 is first withdrawn from tissue, the vacuum is released to de-capture thin area 94 of the esophagus 90, the vacuum chamber 55 is pulled distally to close into the flexible shaft 32, and the endoscope 80 and surgical device 25 are removed from the patient.

Figure 10:
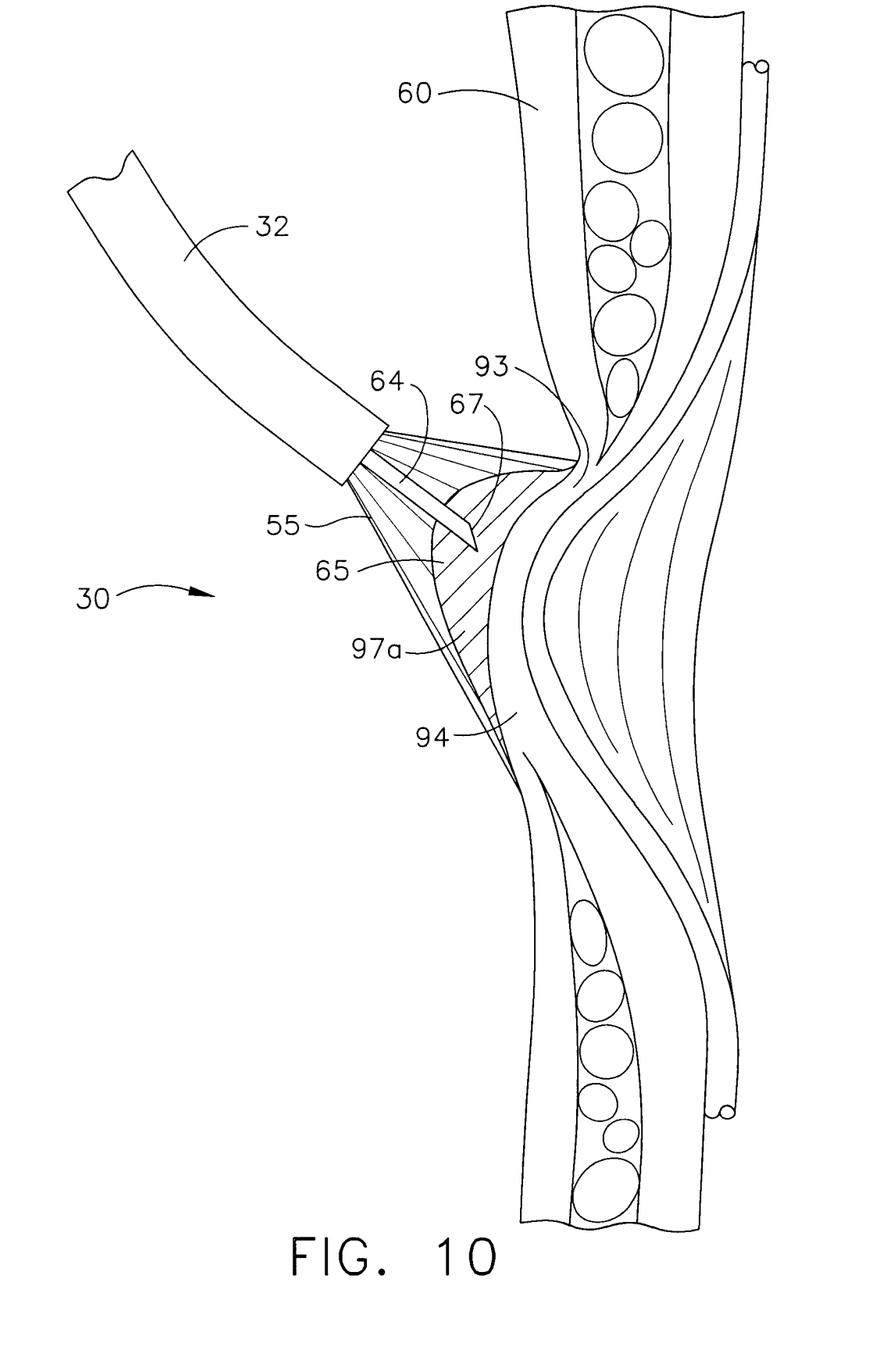
FIG. 10 illustrates an alternate method to stop the bleeders where an adhesive barrier is being placed over the bleeders and the varices.

FIG. 10 shows an alternate method of sealing a bleeder with surgical device 25 and adhesive 65. In this view, the thin area 94 is drawn into vacuum chamber 55 with vacuum, and adhesive 65 is pumped over the surface of mucosal layer 93. When adhesive 65 sets from moisture in the tissue, it forms an exterior protective cap 97a within the esophagus 90. Once protective cap 97a is formed, the bleeders are stopped, a protective bandage or barrier is in position to prevent acid reflux irritation, the barrier promotes healing, and the protective cap 97a re-strengthens the area to prevent varices 95 from protruding into esophagus 90 when the patient coughs or vomits.

Alternate Embodiments

Figure 11:
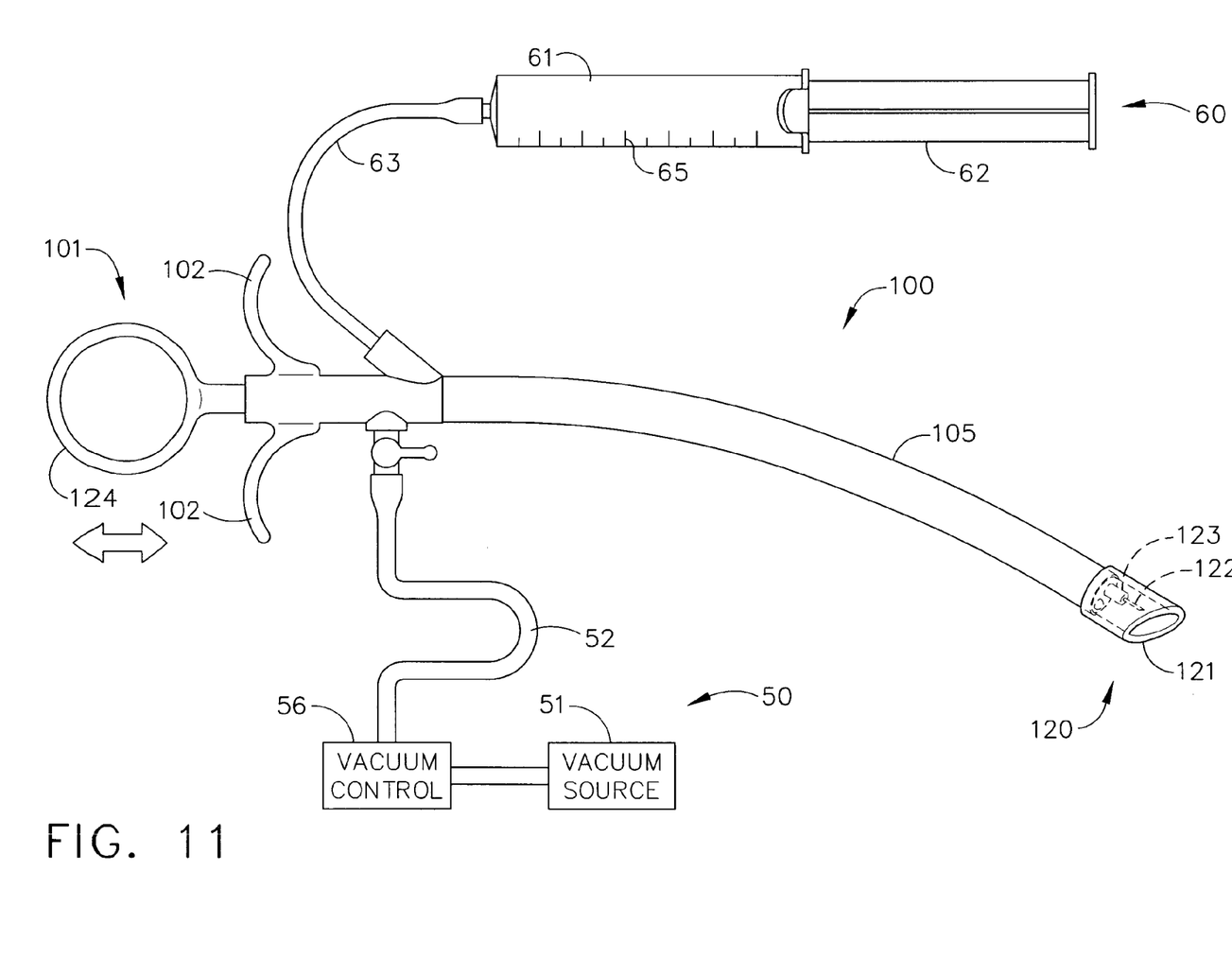
FIG. 11 is an isometric view of an alternate surgical device that can be used without an endoscope.

An alternate embodiment of this device could be used for laparoscopic or arthroscopic surgeries rather than with surgeries that require placement into an endoscope 80. FIG. 11. shows a handheld surgical device 100 having a treatment head 120 suitable for placement at a desired surgical location. Treatment head 120 is well suited for use in open surgeries as well as being sized to fit within a laparoscopic trocar cannula or into a small incision for endoscopic or laparoscopic surgeries. The surgical device 100 has a flexible or malleable shaft 105 attached to treatment head 120 and a handle 101. Grips 102 are fixedly attached to handle 101 for the surgeon to grasp. Vacuum source 51 and vacuum control 56 provide vacuum to treatment head 120 to draw tissue therein, the vacuum conducted through vacuum cannula 52 and shaft 105 to a cylindrical vacuum head 121. Vacuum head 121 is clear so the surgeon can view inside during use. An alternate applicator tip 122 is located within treatment head 120 and is attached to a longitudinally moveable applicator cannula 123.

Applicator cannula 123 is operably attached to a longitudinally moveable control 124 such that proximal and distal motion of control 124 results in proximal and distal motion of applicator cannula 123 and alternate applicator tip 122. Adhesive system 60 contains adhesive 65 in an adhesive reservoir 61 and is operably attached to applicator cannula 123 by cannula 67. Activation of pump 62 moves adhesive 65 from adhesive reservoir 61 into cannula 67, into applicator cannula 123, and dispenses adhesive 65 from alternate applicator tip 122. A sharp 122a can be placed on a distal end of alternate applicator tip 122. Alternately, by way of example, surgical device 100 could use an expanding and contracting vacuum chamber 55 rather than a fixed vacuum head 121.

Figure 12:
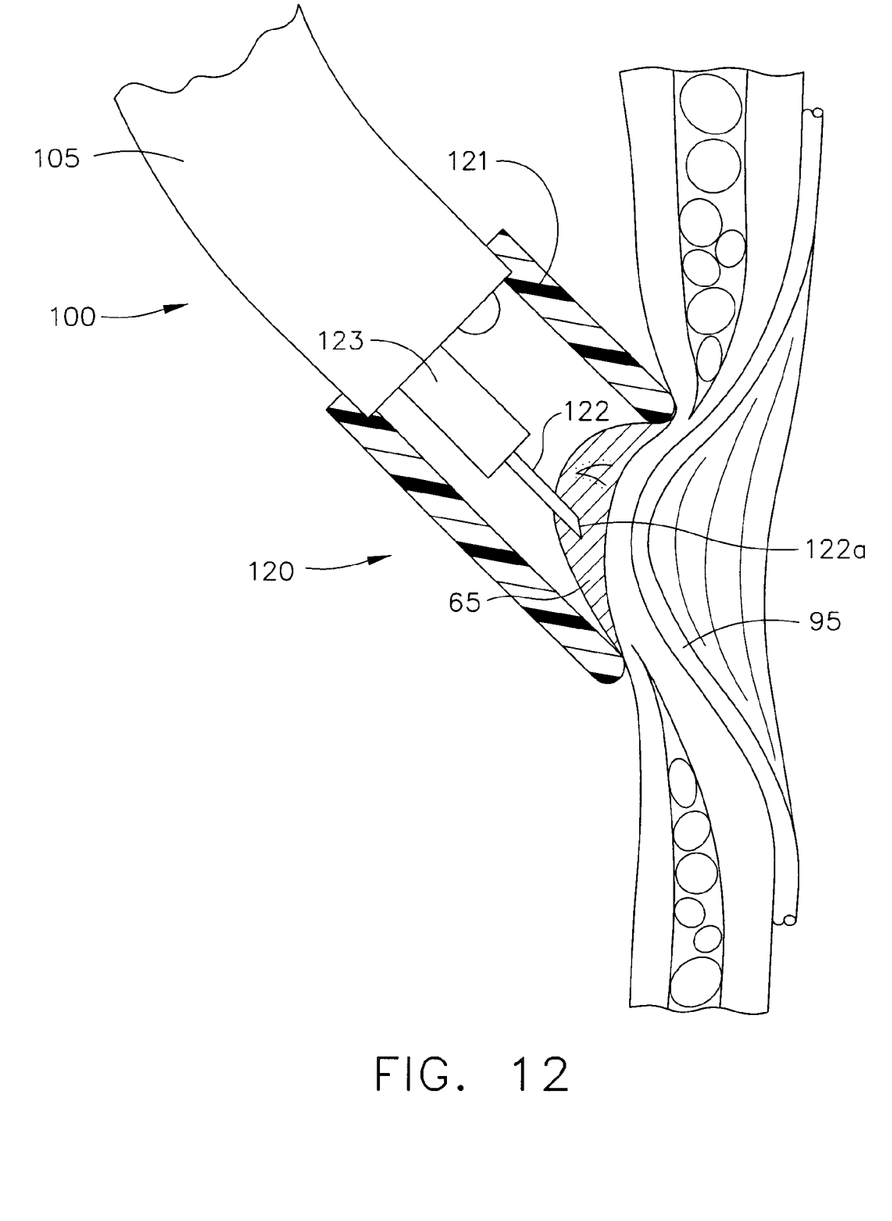
FIG. 12 is a side view of a partial cross section of a vacuum head of the alternate surgical device of FIG. 11 placing an adhesive on tissue.

An example of treatment using surgical device 100 would involve inserting the surgical device 100 into a patient through a trocar cannula. As shown in FIG. 12, the device is moved to a desired site to treat one of a number of varices 95. The vacuum head 121 is placed at the desired site and vacuum is applied from vacuum source 51 to draw tissue therein. The surgeon maneuvers the endoscope to view the site through the clear vacuum head 121 (not shown) and has decided to extend the alternate applicator tip 122 close to the tissue rather than pierce the tissue with sharp 122a. Adhesive 65 is being applied over the varices 95 to staunch the bleeding.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, the adhesives listed are merely exemplary and many other adhesives and chemical compounds fall within the scope of the present invention.

What is claimed is:

1. A surgical device for staunching the flow of blood from tissue, the surgical device comprising:
 a) an adhesive implantable in a patient's body;
 b) a vacuum system for capturing tissue therein, the vacuum system comprising:
  (i) a flexible shaft, wherein the flexible shaft has a distal end,
  (ii) a vacuum cannula, wherein the vacuum cannula is disposed within and runs parallel to the flexible shaft, wherein the vacuum cannula is slidable within the flexible shaft, and
  (iii) a vacuum head disposed at the distal end of the vacuum cannula, wherein the vacuum head is configured to form a vacuum chamber for the reception of tissue therein, wherein the vacuum cannula and the vacuum head are configured to advance together from an interior position within the flexible shaft to an exterior position where the vacuum head is located distal to the distal end of the flexible shaft,
   wherein the vacuum head is configured to collapse in the interior position to a collapsed configuration, wherein the vacuum head is configured to expand to an expanded configuration in the exterior position when extended from the distal end of the flexible shaft,
   wherein the vacuum head has a first circumference in the expanded configuration, wherein the distal end of the flexible shaft has a second circumference, and wherein the first circumference is greater than the second circumference; and
 c) an adhesive system for applying the adhesive to tissue captured within the vacuum system to staunch the flow of blood, the adhesive system comprising an adhesive cannula, wherein the adhesive cannula is coaxially disposed within and runs parallel to the vacuum cannula, wherein the adhesive system comprises an adhesive tip at a distal end of the adhesive cannula, wherein the adhesive cannula is movable relative to the vacuum cannula such that the adhesive cannula is operable to move the adhesive tip from a first position within the vacuum cannula and proximal to the distal end of the flexible shaft to a second position distal of the flexible shaft, wherein the vacuum system and the adhesive system are configured and positioned relative to each other such that the adhesive system is operable to apply the adhesive to tissue captured within the vacuum system and thereby form a protective cap with the adhesive to staunch the flow of blood from the tissue captured within the vacuum system.

2. The surgical device of claim 1 wherein the adhesive is polymerizable.

3. The surgical device of claim 2 wherein the adhesive is one or more selected from the group of:
 a) a polymerizable monomer,
 b) a polymerizable 1,1,1,1-disubstituted ethylene monomer, and
 c) a cyanoacrylate formulation.

4. The surgical device of claim 2 wherein a polymerization agent for the adhesive is one or more of the polymerization agents selected from the group consisting of:
 a) natural body moisture,
 b) saline, and
 c) an adhesion initiator compound.

5. The surgical device of claim 1 wherein the vacuum system further comprises a vacuum source attachable to the surgical device.

6. The surgical device of claim 1 wherein the vacuum head has a third circumference in the collapsed configuration, wherein the third circumference is less than the second circumference.

7. The surgical device of claim 6 wherein the vacuum head is transparent.

8. The surgical device of claim 6 wherein the vacuum head is a cone in the expanded position.

9. The surgical device of claim 6 wherein the vacuum head is constructed from at least one piece of spring material having a natural position, wherein the natural position is selected from the group consisting of:
 a) a naturally open position,
 b) a naturally partially open position, and
 c) a naturally closed position.

10. The surgical device of claim 9 wherein the at least one piece of spring material has at least one fold.

11. The surgical device of claim 9 wherein the at least one piece of spring material is on or more spring material selected from the group consisting of:
   a) nitinol,
   b) mylar,
   c) polytetraflouroethylene,
   d) nylon, and
   e) silicone.

12. The surgical device of claim 6 wherein the vacuum head is an openable and closable umbrella having at least one rib structure and at least one deformable film operably attached to the at least one rib structure.

13. The surgical device of claim 12 wherein the at least one rib structure is selected from the group consisting of:
   a) a rigid folding rib structure,
   b) a deformable spring rib structure,
   c) a rib structure molded as a thicker part of the deformable film, and
   d) a spring attached to a folding rib structure to open the folding rib structure.

14. The surgical device of claim 12 wherein the at least one deformable film is constructed from one or more materials selected from the group consisting of: natural rubber, artificial rubber, polyethelene, polypropelene, polytetraflouroethylene, paper, and surgical fabric.

15. The surgical device of claim 6 wherein the adhesive system further comprises a pump, wherein the adhesive cannula is operatively attached between the pump and the vacuum chamber, wherein when the adhesive system is actuated, the pump is operable to deliver adhesive to tissue captured within the vacuum system through the adhesive cannula.

16. The surgical device of claim 15 wherein the adhesive tip is operably disposed within the vacuum head, the adhesive tip having a discharge port for applying adhesive to tissue and being moveable within the vacuum head towards and away from tissue captured within the vacuum head.

17. The surgical device of claim 16 wherein the adhesive tip has a sharp tip for piercing tissue, wherein the discharge port is located in the sharp tip for dispensing adhesive into tissue captured within the vacuum system.

18. The surgical device of claim 15 wherein the adhesive system includes one or more chemical agents applied with the adhesive to tissue within the vacuum chamber, wherein the chemical agent is one or more chemical agents selected from the group consisting of: an adhesive initiator, an image enhancement media, an anesthetic, a sclerotic agent, a necrosing agent, a drug, and a medicament.

19. The surgical device of claim 18 wherein the adhesive system further comprises a mixer between the pump and the discharge port, wherein the mixer mixes the chemical agent with the adhesive prior to applying the mixture of adhesive and chemical agent to tissue captured in the vacuum head.

* * * * *